United States Patent [19]

Beppu et al.

[11] Patent Number: 5,654,180
[45] Date of Patent: Aug. 5, 1997

[54] HYBRID PLASMID VECTORS, RECOMBINANT PLASMIDS CONTAINING GENES ENCODING NITRILE DEGRADING ENZYMES, TRANSFORMANTS CONTAINING THE RECOMBINANT PLASMIDS AND METHODS OF PRODUCING AMIDES AND ACIDS USING THE TRANSFORMANTS

[75] Inventors: Teruhiko Beppu, 5-21, Horinouchi 1-chome, Suginami-ku, Tokyo; Sueharu Horinouchi; Makoto Nishiyama, both of Tokyo; Fujio Yu, Yokohama; Yoshihiro Hashimoto, Tokyo, all of Japan

[73] Assignees: Nitto Chemical Co. Ltd.; Teruhiko Beppu, both of Japan

[21] Appl. No.: 344,683

[22] Filed: Nov. 17, 1994

Related U.S. Application Data

[63] Continuation of Ser. No. 196,823, Feb. 15, 1994, abandoned, which is a continuation of Ser. No. 845,287, Mar. 3, 1992, abandoned.

[30] Foreign Application Priority Data

Mar. 4, 1991 [JP] Japan .................. 3-037544
Mar. 4, 1991 [JP] Japan .................. 3-037545

[51] Int. Cl.$^6$ ............... C12P 13/02; C12P 7/40; C12N 1/20; C12N 15/74
[52] U.S. Cl. ............ 435/139; 435/136; 435/252.3; 435/252.33; 435/320.1
[58] Field of Search .............. 435/320.1, 252.3, 435/252.33, 129, 136

[56] References Cited

U.S. PATENT DOCUMENTS

| 4,920,054 | 4/1990 | Kozlowski et al. | 435/252.31 |
| 5,246,857 | 9/1993 | Yu et al. | 435/320.1 |

FOREIGN PATENT DOCUMENTS

| 0 445 646 | 9/1991 | European Pat. Off. | C12N 15/53 |
| 2 633 938 | 1/1990 | France | C12N 15/55 |
| WO89/07151 | 8/1989 | WIPO | C12P 21/00 |

OTHER PUBLICATIONS

Singer et al. (Feb. 1988), J. Bacteriol. 170(2): 638–645.
Ikehata et al. (1989), Eur. J. Biochem. 181: 563–570.
Hashimoto et al. (1991), Biochim Biophys. Acta 1088 (2): 225–233 [Chem. Abstracts 115, No. 107240y (1991)]Abstract only is provided.

*Primary Examiner*—Jasemine C. Chambers
*Assistant Examiner*—Scott D. Priebe
*Attorney, Agent, or Firm*—Pennie & Edmonds

[57] ABSTRACT

The present invention provides a recombinant plasmid comprising combining a hybrid plasmid vector with the isolated DNA sequences of one or more genes encoding nitrile degrading enzymes which are derived from bacteria belonging to the genus Rhodococcus, said hybrid plasmid vector comprising an isolated DNA sequence which confers on the vector the ability to replicate and amplify in the cells of bacteria belonging to the genus Rhodococcus, and an isolated DNA sequence which confers on the vector the ability to replicate and amplify in the cells of bacteria belonging to *Escherichia coli*, and an isolated DNA sequence containing a drug resistance gene.

19 Claims, 5 Drawing Sheets

HYBRID PLASMID VECTORS, RECOMBINANT PLASMIDS CONTAINING GENES ENCODING NITRILE DEGRADING ENZYMES, TRANSFORMANTS CONTAINING THE RECOMBINANT PLASMIDS AND METHODS OF PRODUCING AMIDES AND ACIDS USING THE TRANSFORMANTS

This is a continuation of application Ser. No. 08/196,823, filed Feb. 15, 1994, now abandoned, which is a continuation of application Ser. No. 07/845,287, filed Mar. 3, 1992, now abandoned.

BACKGROUND OF THE INVENTION

The present invention relates to novel hybrid plasmid vectors, recombinant plasmids containing a nitrile hydratase gene and an amidase gene, transformants that are made by transforming bacteria belonging to the genus Rhodococcus or Escherichia with the recombinant plasmids and to methods of producing amides and acids.

Microorganisms belonging to the genus Rhodococcus are known to hydrate or hydrolyze nitriles to produce amides or acids (EP Publication No. 0188316, 0204555, and 0348901). In addition, microorganisms belonging to *Rhodococcus rhodochrous* are known to have a high hydration activity of nitriles (EP Publication No. 0307926). These useful properties of the microorganisms have motivated to develop a host-vector system to utilize bacteria belonging to the genus Rhodococcus. In reality, vectors suitable to host bacteria belonging to the genus Rhodococcus have not been appreciably developed yet. Very few suitable plasmid vectors have been found from *Rhodococcus sp.* H13-A [J.Bacteriol. 170:638-645 (1988)], *Rhodococcus erythropolis* (*rhodochrous*) ATCC12674 [Mol.Gen. Genet., 211:148-154 (1988)] and *Rhodococcus rhodochrous* ATCC 4276 which was disclosed by the present inventors in Japanese Patent Application No. 270377/1990. The development of novel vectors which are derived from the genus Rhodococcus and industrially useful in culturing microorganisms or in improving the properties of microorganisms, has been awaited.

The present inventors have isolated genes encoding nitrile degrading enzymes from bacteria belonging to the genus Rhodococcus, cloned the genes into vectors derived from *Escherichia coli* and investigated the gene expression in *Escherichia coli* hosts. The enzymes having a sufficient enzymatic activity have not been produced in *Escherichia coli* hosts so far [Eur.J.Bichem. 181:563-570 (1989), Biochem.Biophys.Acta., 1088: 225-233 (1991)].

Industrially useful, covalently closed circular plasmids derived from bacteria belonging to the genus Rhodococcus are potentially suitable plasmids to genetically improve the desirable properties of the genus Rhodococcus hosts. These plasmids, however, do not contain drug resistance genes to be used as a marker. Suitable plasmid vectors could be constructed by introducing a marker gene into the plasmids. There is a single example that is described in J. Bacteriol. 170: 638-645, 1988.

We have successfully constructed shuttle vectors suitable for industrial use by inserting drug resistance genes to be used as a marker, cloning sites and genes necessary for replication in *Escherichia coli* into covalently closed circular plasmids such as pRC001, pRC002. pRC003 and pRC004. We have subsequently subcloned the gene of a clone encoding a nitrile degradation enzyme into the shuttle vectors to give recombinant plasmids, transformed bacteria belonging to the genus Rhodococcus or Escherichia with the recombinant plasmids and produced amides and acids using the transformants.

SUMMARY OF THE INVENTION

A first invention provides a hybrid plasmid vector comprising (A) an isolated DNA sequence which is derived from a plasmid selected from the group consisting of pRC001, pRC002, pRC003 and pRC004 and which confers the vector the ability to replicate and amplify in the cells of bacteria belonging to the genus Rhodococcus, and (B) an isolated DNA sequence which confers the vector the ability to replicate and amplify in the cells of bacteria belonging to *Escherichia coli*, and (C) an isolated DNA sequence containing a drug resistance gene.

A second invention provides a recombinant plasmid comprising combining a hybrid plasmid vector with the isolated DNA sequences of one or more genes encoding nitrile degrading enzymes which are derived from bacteria belonging to the genus Rhodococcus, said hybrid plasmid vector comprising an isolated DNA sequence which confers the vector the ability to replicate and amplify in the cells of bacteria belonging to the genus Rhodococcus, and an isolated DNA sequence which confers the vector the ability to replicate and amplify in the cells of bacteria belonging to *Escherichia coli*, and an isolated DNA sequence containing a drug resistance gene.

The hybrid plasmid vectors are useful for culturing microorganisms belonging to the genus Rhodococcus or Escherichia to be industrially used and for improving the properties of the microorganisms.

The present invention provides transformants that contain a number of genetically engineered recombinant plasmids capable of converting nitriles to amides and acids so that the method of the present invention is more efficient in producing amides and acids than conventional methods.

DETAILED DESCRIPTION OF THE INVENTION

Figure 1:
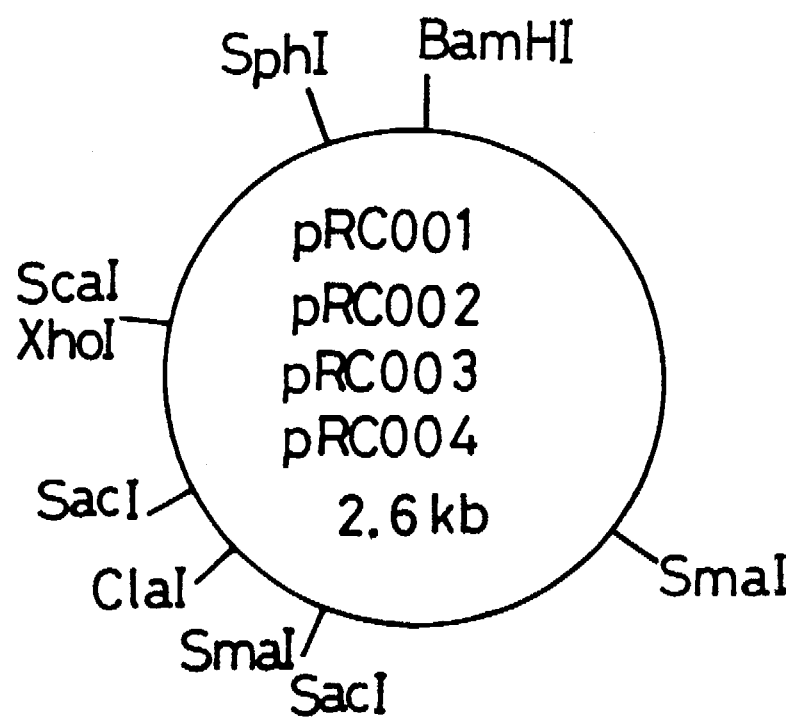
FIG. 1 shows a restriction map of pRC001, pRC002. pRC003 or pRC004.

The isolated DNA sequence that confers on plasmid vectors the ability to replicate and amplify in the cells of bacteria belonging to the genus Rhodococcus may be a whole or a part of plasmid selected from the group consisting of pRC001, pRC002. pRC003 and pRC004.

pRC001, pRC002. pRC003 and pRC004 are derived from *Rhodococcus rhodochrous* ATCC4276, ATCC14349, ATCC14348 and IFO3338, respectively. The restriction map of these plasmids is shown in FIG. 1.

The isolated DNA sequence that confers on plasmid vectors the ability to replicate and amplify in the cells of bacteria belonging to *Escherichia coli* may be a whole or a part of plasmid selected from the group consisting of pHSG299, pHSG298, pUC19 and pUC18.

Suitable marker genes which are expressed in hosts such as bacteria belonging to the genus Rhodococcus and the genus Escherichia and capable of conferring the hosts drug resistance may be a kanamycin resistant gene or a ampicillin resistant gene. Any drug resistance genes or more than one drug resistance gene may be incorporated into plasmid vectors as a marker as long as the presence of the desired plasmid is indicated by the marker.

Host bacteria for the hybrid plasmid vectors of the present invention may be *Rhodococcus rhodochrous* ATCC12674 in the genus Rhodococcus and *Escherichia coli* K-12 strains in the genus Escherichia. These bacteria can be transformed with the hybrid plasmid vectors.

The recombinant plasmid of the present invention comprises hybrid plasmid-vectors such as pK1, pK2, pK3, pK4 and pA3. *Rhodococcus rhodochrous* ATCC12674 was transformed with the hybrid plasmid vectors. The transformants were deposited with Fermentation Research Institute, Agency of Industrial Science and Technology and were assigned the accession number as follows:

|  | accession number |
|---|---|
| *Rhodococcus rhodochrous* ATCC 12674/pK1 | FERM BP-3728 |
| *Rhodococcus rhodochrous* ATCC 12674/pK2 | FERM BP-3729 |
| *Rhodococcus rhodochrous* ATCC 12674/pK3 | FERM BP-3730 |
| *Rhodococcus rhodochrous* ATCC 12674/pK4 | FERM BP-3731 |
| *Rhodococcus rhodochrous* ATCC 12674/pA3 | FERM BP-3732 |

Genes encoding nitrile degradation enzymes may be nitrile hydratase and/or amidase genes.

Any medium components used to grow microorganisms may be used to culture the transformants. Such medium components include carbon sources such as saccharides, e.g., glucose, fructose, sucrose, maltose, organic acids such as acetic acid and citric acid, alcohols such as ethanol and glycerol, natural nitrogen source such as peptone, meat extract, yeast extract, hydrolyzed proteins, and amino acids, and various inorganic or organic ammonium salts and, if necessary, inorganic salts, a trace amount of metal salts, and vitamins.

Microorganisms described above are cultured by methods known in the art: pH 4–10, at 20°–45° C., aerobic conditions, 10–96 hours of incubation. Transformants obtained from culture are used to convert nitrile to amide or acid by the following methods; substrates are added to the suspension of the bacterial cells harvested by centrifugation of the culture; substrates are added to the suspension of the treated bacterial cells (e.g., disrupted bacterial cells, a crude or purified enzyme extract and the like), or to the immobilized bacterial cells by methods known in the art; substrates are added to the culture of the transformants while they grow.

Nitriles used as substrates are represented by the general formula, R—(CN)n, wherein n is 1 (mononitrile) to more than 2 (polynitrile), R is hydrogen, saturated or unsaturated hydrocarbon residues having various numbers of a carbon atom in a straight chain, a branched chain, or a cyclic form, an amino group, an hydroxyl group, halogen, a carboxyl group, or hydrocarbon residues having substituents. Nitriles include a wide range of compounds, such as acetonitrile, propionitrile, n-butyronitrile, isobutyronitrile, n-valeronitrile, acrylonitrile, methacrylonitrile, benzonitrile, cyanopyridine, malononitrile, succinonitrile, fumaronitrile, chloroacetonitrile, β-hydroxypropionitrile, aminoacetonitrile and β-aminopropionitrile and the like. The reaction is typically carried out under conditions wherein the substrate concentration is 0.1–10% (w/v), the bacterial cell density in culture is 0.01–10% (w/v) and the pH is 4–10.

EXAMPLE

The present invention will be further illustrated by the Examples, which do not limit the scope of the present invention.

Example 1

(1) Construction of Hybrid Plasmid Vectors, pK1, pK2, pK3, and pK4 by Combining pRC001, pRC002. pRC003 or pRC004 with pHSG299

Figure 2:
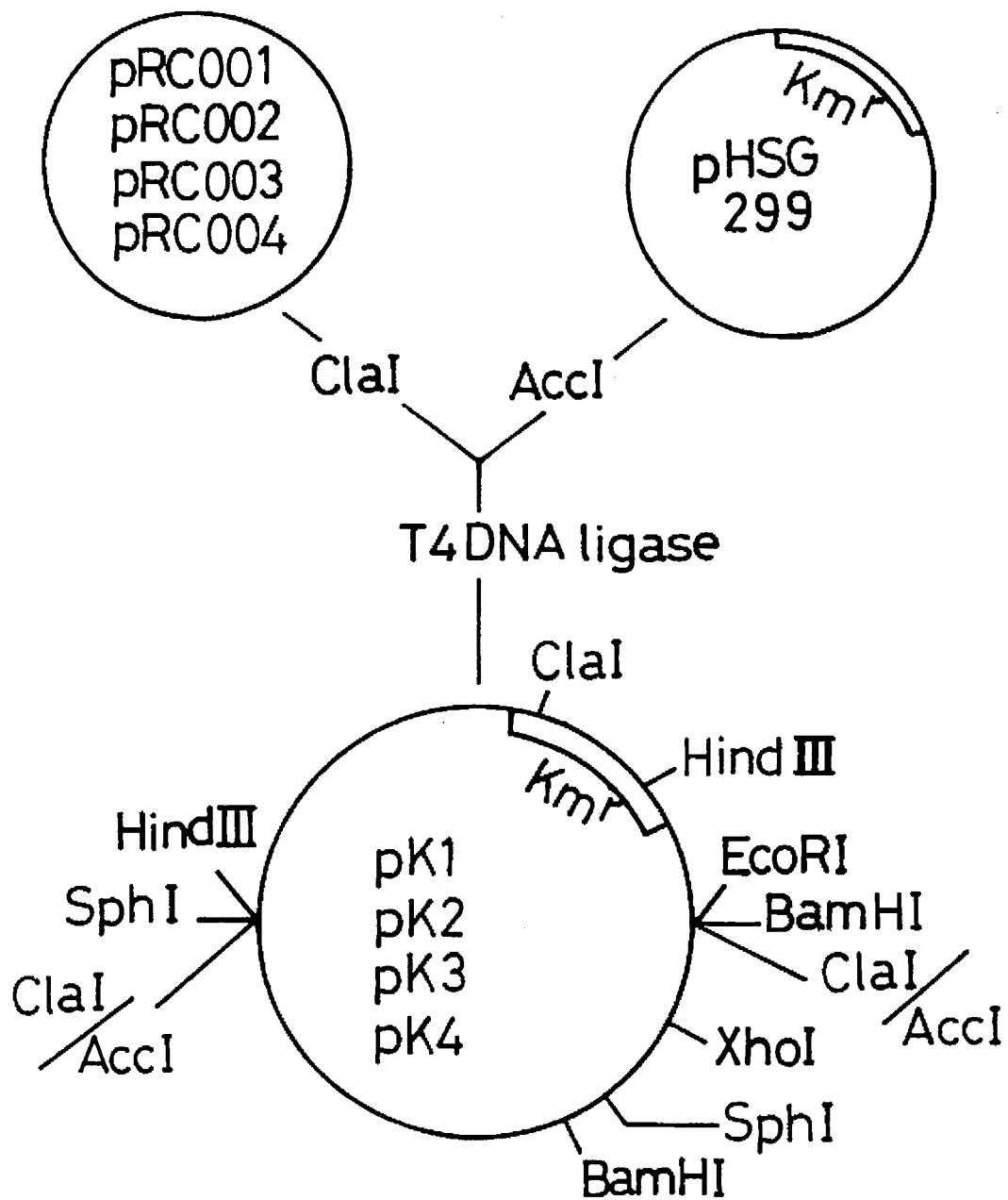
FIG. 2 shows a construction of pK1, pK2, pK3, and pK4.

Hybrid plasmid vectors, pK1, pK2, pK3, and pK4, were constructed as is shown in FIG. 2. The DNAs of pRC001, pRC002, pRC003 and pRC004, 1 μg each, were digested with restriction enzyme, ClaI (5 units), at 37° C. for one hour. 0.5 μg of pHSG299 DNA(TAKARA SHUZO CO., LTD), which is 2.7 kb in size and kanamycin resistant, was digested with 5 units of AccI at 37° C. for one hour. After digestion, 1/10 volume of 1M Tris-HCl/pH9.0 was added to both reaction mixtures, which were then dephosphorylated with 1 unit of alkaline phosphatase at 65° C. for one hour. The dephosphorylated restriction fragments were electrophoresed along with HindIII digested λ phage DNA as a marker on a 0.7% agarose gel. After electrophoresis, the 2.6 kb bands of pRC001, pRC002, pRC003 and pRC004 and the 2.7 kb band of pHSG299 were cut out from the gel. DNA was recovered using Gene Clean Kit (FUNAKOSHI K.K.) and dissolved in TE buffer (10 mM Tris-HCl, 1 mM EDTA, pH8.0). Each of pRC001, pRC002, pRC003 or pRC004 DNA solution was combined with an equal amount of a pHSG299 DNA solution. T4 DNA ligase, ATP, dithiothreitol and $MgCl_2$ were added to the mixtures (final concentration in a mixture: 1 unit of T4 DNA ligase, 1 mM ATP, 10 mM dithiothreitol and 10 mM $MgCl_2$). The ligation mixture was the incubated at 4° C. overnight. After incubation, the ligation product was added to the suspension of *Escherichia coli* JM 105 competent cells (TAKARA SHUZO CO., LTD) and the mixture was incubated on ice for one hour. The mixture was heat-shocked at 42° C. for 2 minutes and a 2xYT medium (0.5% NaCl, 1% yeast, 1.6% tryptone) was added to the mixture. The mixture was then incubated with shaking at 37° C. for one hour. After incubation, the mixture was spread on a 2xYT agar plate containing 1 mM IPTG (isopropyl-β-galactoside) and 0.02% X-gal (5-bromo-4-chloro-3-indolyl-β-D-galactopyranoside). The plate was incubated at 37° C. overnight. Colonies were grown on the plate. White colonies were picked and grown in 3 ml of a 2xYT medium containing 50 μg/ml of kanamycin at 37° C. for 8 hous. After growth, bacterial cells were harvested by centrifugation at 15,000 rpm for 5 minutes. The bacterial cells were then suspended in 0.35 ml of a STET solution (8% sucrose, 0.5% Triton X-100, 50 mM EDTA, 10 mM Tris-HCl, pH8.0). 25 μl of lysozyme (10 mg/ml) was added to the suspension. The suspension was vortexed for 3 seconds, placed in a boiling water bath for 50 seconds and centrifuged at 15,000 rpm for 15 minutes. The supernatant was saved. 0.5 ml of 1:1 TE-saturated phenol/chloroform was added to the supernatant. The mixture was vortexed and then centrifuged at 15,000 rpm for 5 minutes. The top portion was saved. 0.5 ml of diether was added to the top portion and the mixture was vortexed. The mixture was then centrifuged and the top portion was discarded. 0.5 ml of isopropanol and 50 µl of 2.5M sodium acetate /pH 4.5 were added to the bottom portion. The mixture was incubated at −80 °C. for 30 minutes. After incubation, the mixture was centrifuged at 15,000 rpm for 10 minutes. The pellet was rinsed with 70% ethanol, vaccuum dried and resuspended in 0.1 ml of TE buffer. The DNA solution was digested with HindIII, BamHI, SphI, EcoRI and XhoI and a restriction map was constructed. The hybrid plasmids constructed from pRC001, pRC002, pRC003 and pRC004 and pHSG299 were termed pK1, pK2, pK3, and pK4.

These plasmids have identical restriction sites as is shown in Table 1.

TABLE 1

Hybrid plasmids (pK1, pK2, pK3, pK4)

| Restriction enzyme | Number of sites | Molecular weight (kb) |
| --- | --- | --- |
| EcoRI | 1 | 5.3 |
| BamHI | 2 | 4.4 1.0 |
| ClaI | 1 | 5.3 |
| HindIII | 2 | 3.3 2.0 |
| SphI | 2 | 3.6 1.7 |
| XhoI | 1 | 5.3 |

(2) Isolation and Purification of Hybrid Plasmids, pK1, pK2, pK3, and pK4

The kanamycin resistance transformants [*Escherichia coli* JM105 (pK1), *Escherichia coli* JM105 (pK2), *Escherichia coil* JM105 (pK3), *Escherichia coli* JM105 (pK4)] were grown in 200 ml of a 2xYT medium. After growth, bacterial cells were harvested by centrifugation, washed with 40 ml of TES buffer (10 mM Tris-HCl/pH 8.0, 10 mM NaCl, 1 mM EDTA) and resuspended in 8 ml of a STET solution (50 mM Tris-HCl/pH8.0, 5 mM EDTA, 35 mM sucrose). 10 mg of lysozyme was added to the suspension and the mixture was shaken at 0° C. for 5 minutes. 4 ml of 0.25M EDTA/pH8.0 was added to the mixture. The mixture was then incubated at 0° C. for 5 minutes with occasional gentle swirling. The mixture was then left standing at room temperature. 2 ml of 10% SDS (sodium dodecyl sulfate) and 5 ml of 5M NaCl were added to the mixture. The mixture was incubated at 4° C. for 3–12 hours. After incubation, the mixture was centrifuged at 65,000 ×g at 4° C. for one hour. 4.6 ml of 50% polyethylene glycol (6,000) was added to the supernatant. The mixture was incubated on ice for 3 hours. The mixture was then centrifuged at 1,000×g for 5 minutes. The pellet was resuspended in 7.5 ml of TES. 8.2 g of CsCl and 0.2 ml of ethidium bromide (15 mg/ml) was added to the suspension. The mixture was subjected to density gradient centrifugation at 130,000×g for 42 hours. After centrifugation, the plasmid portion was removed under the irradiation of UV light. The plasmid portion was extracted with n-butanol to remove ethidium bromide. The plasmid extract was dialyzed against TE. Plasmid DNA was precipitated with ethanol. The presence of the desired plasmid DNA was confirmed by electrophoresis on a 0.7% agarose gel.

(3) Introduction of Hybrid Plasmids, pK1, pK2, pK3, and pK4 into bacteria belonging to the genus Rhodococcus The bacteria cells of *Rhodococcus rhodochrous* ATCC 12674 at a log phase in growth were harvested by centrifugation, washed 3 times with ice cold sterilized water and resuspended in a 15% PEG(6,000) solution (cell density: more than $10^9$ cells/ml). The hybrid plasmid DNAs, 0.01 µg each, were combined with 10 µl of the bacterial cell suspension. The mixture was incubated on ice and then placed in the chamber 11 of a cell fusion apparatus (SHIMAZU Corp., SSH-1). The chamber was cooled and the mixture was subjected to electroporation at a pulse amplitude of 500 µs at an electric field strength of 14 kv/cm.

After electroporation, the mixture was incubated at 0° C. for 10 minutes and then at 37° C. for 5 minutes. After incubation, 1 ml of an MY medium was added to the mixture. The mixture was incubated at 25° C. for 3 hours. The mixture was then spread on an MY agar medium plate containing 50 µg/ml of kanamycin. The plate was incubated at 25° C. for 3–6 days. After incubation, colonies appeared on the plate. These colonies were spread on an MY agar medium plate containing 50 µg/ml of kanamycin again to confirm that the colonies were kanamycin resistant.

On Mar. 1, 1991, cultures of the following microorganisms were deposited with the FERMENTATION RESEARCH INSTITUTE (FRI), AGENCY OF INDUSTRIAL SCIENCE AND TECHNOLOGY, MINISTRY OF INTERNATIONAL TRADE AND INDUSTRY, at 1–3 Higashi 1-chrome, Tsukuba-shi, Ibaraki-ken, 305 Japan and assigned accession numbers as set forth below:

| | accession number |
| --- | --- |
| *Rhodococcus rhodochrous* ATCC 12674/pK1 | FERM BP-3728 |
| *Rhodococcus rhodochrous* ATCC 12674/pK2 | FERM BP-3729 |
| *Rhodococcus rhodochrous* ATCC 12674/pK3 | FERM BP-3730 |
| *Rhodococcus rhodochrous* ATCC 12674/pK4 | FERM BP-3731 |

The properties of pK4 are further investigated as described below.

(4) Isolation and Purification of the Hybrid Plasmid Vector from the Rhodococcus Transformant

*Rhodococcus rhodochrous* ATCC 12674/pK4 was grown in 400 ml of an MY medium containing 50 µg/ml of kanamycin. When the $OD_{660}$ of the culture reached 0.15–0.2, 0.5 U/ml of penicillin G was added to the culture. The culture was further incubated until the $OD_{660}$ of the culture reached at 1.0. Bacterial cells were harvested by centrifugation, washed with 40 ml of TES and resuspended in 11 ml of a solution (50 mM of Tris-HCl/pH8.0, 12.5% sucrose, 100 mM NaCl, 1 mg/ml of lysozyme). The suspension was incubated with shaking at 37° C. for 3 hours. 0.6 ml of 0.5M EDTA, 2.4 ml of 5M NaCl and 4.4 ml of 4% SDS-0.7M NaCl were added to the suspension in this order. The mixture was gently swirled and incubated on ice for 18 hours. The mixture was centrifuged at 65,000×g at 4° C. for one hour. After centrifugation, 4.6 ml of 50% polyethylene glycol was added to the supernatant. The mixture was incubated on ice for 3 hours. The mixture was then centrifuged at 1,000×g for 5 minutes. The pellet was resuspended in 5 ml of TES. 7.5 g of CsCl and 2 ml of TES containing 1.5 mg/ml of ethidium bromide were added to the suspension. The mixture was subjected to density gradient centrifugation at 130,000×g for 42 hours. After centrifugation, the plasmid portion was removed under the irradiation of UV light. The plasmid portion was extracted with n-butanol to remove ethidium bromide. The plasmid extract was dialyzed against TE. Plasmid DNA was precipitated with ethanol. The presence of desired plasmid DNA was confirmed by electrophoresis on a 0.7% agarose gel.

(5) Comparison between pK4s isolated from the genus Escherichia and Rhodococcus (5)-(i) Molecular Weight A small amount of the plasmid DNAs was electrophoresed along with markers such as pUC18 (2.69 kb), pUC118 (3.16 kb), pBR322 (4.36 kb) on a 0.7% agarose gel. The size of both plasmid DNAs was about 5.3 kb.

(5)-(ii) Restriction Sites

A small amount of the plasmid DNAs was digested with restriction enzymes. The restriction fragments were electrophoresed along with HindIII or PstI digested λ phage DNA as a marker on a 0.7% agarose gel. The band pattern showed that both plasmid DNAs had exactly the same restriction sites as is shown in the Table 1.

(6) Transformation of *Escherichia coli* with pK4 Isolated from Rhodococcus

*Escherichia coli* JM105 was transformed with pK4 isolated from *Rhodococcus rhodochrous* ATCC 12674/pK4. Transformants were screened for kanamycin resistance by culturing on a 2xYT agar medium plate containing 50 µg/ml of kanamycin. Most of them were positive transformants. Plasmid DNA was isolated from 12 of the positive transformants, digested with restriction enzymes and electrophoresed on a agarose gel. The band pattern showed that the isolated plasmid DNA had the same restriction sites as those isolated from pK4 of the genus Rhodococcus transformant.

Example 2

Figure 3:
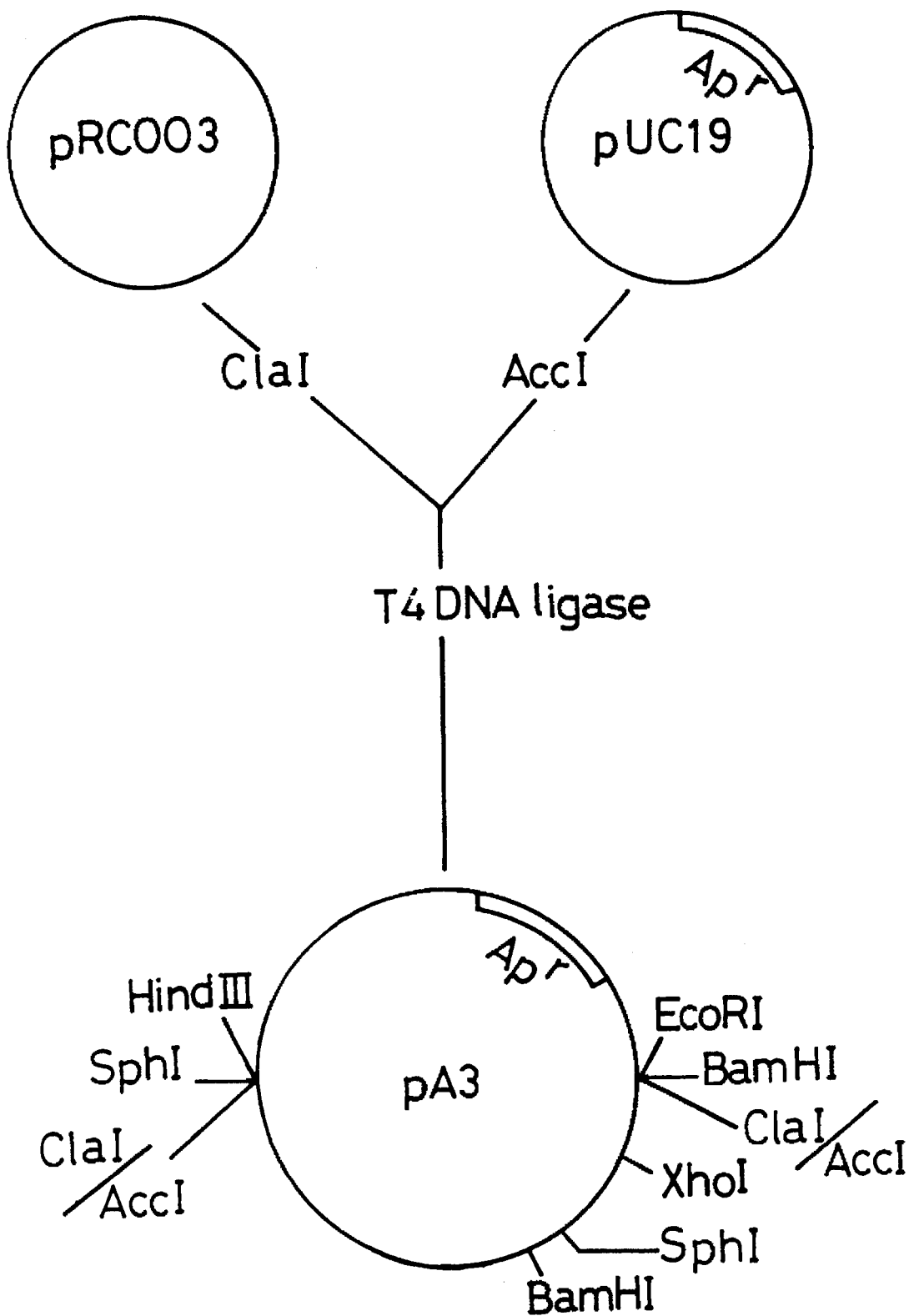
FIG. 3 shows a construction of pA3.

Plasmid pA3 was constructed as is shown in FIG. 3. pRC003 DNA was digested with ClaI and the restriction fragment was inserted into the AccI site of pUC19. The construct was designated as pA3. *Escherichia coli* JM105 was transformed with pA3 as described in the Example 1. The transformants were screened by culturing on a 2xYT agar medium plate containing 50 µg/ml of ampicillin, 1 mM IPTG and 0.2% X-gal. White colonies were picked and grown. Plasmid DNA was isolated, purified, digested with restriction enzymes and analyzed. *Rhodococcus rhodochrous* ATCC 12674 was transformed with the plasmid DNA. The transformant showed that the plasmid DNA conferred ampicillin resistance (10 µg/ml of ampicillin) on the host. The transformant, *Rhodococcus rhodochrous* ATCC 12674/pA3, was deposited with Fermentation Research Institute, Agency of Industrial Science and Technology, and was assigned the accession number FERM BP-3732.

Table 2 shows a restriction enzyme map of pA3.

TABLE 2

| | (pA3) | |
|---|---|---|
| Restriction enzyme | Number of sites | Molecular weight (kb) |
| EcoRI | 1 | 5.3 |
| BamHI | 2 | 4.3, 1.0 |
| ClaI | 0 | — |
| HindIII | 1 | 5.3 |
| SphI | 2 | 3.6, 1.7 |
| XhoI | 1 | 5.3 |

Example 3

(1) Construction of Recombinant Plasmids Containing Nitril Hydratase and Amidase Genes pYUK120 and 121 [Eur. J. Biochem. 181:563–570 (1989)] or pANH101[Biochim. Biophys. Acta 1088: 225–233 (1991)], which contain a DNA fragment which is originally derived from *Rhodococcus sp.* N-774 and cloned into *Escherichia coli*, comprise a nitrile hydratase gene or an amidase gene, respectively.

Figure 4:
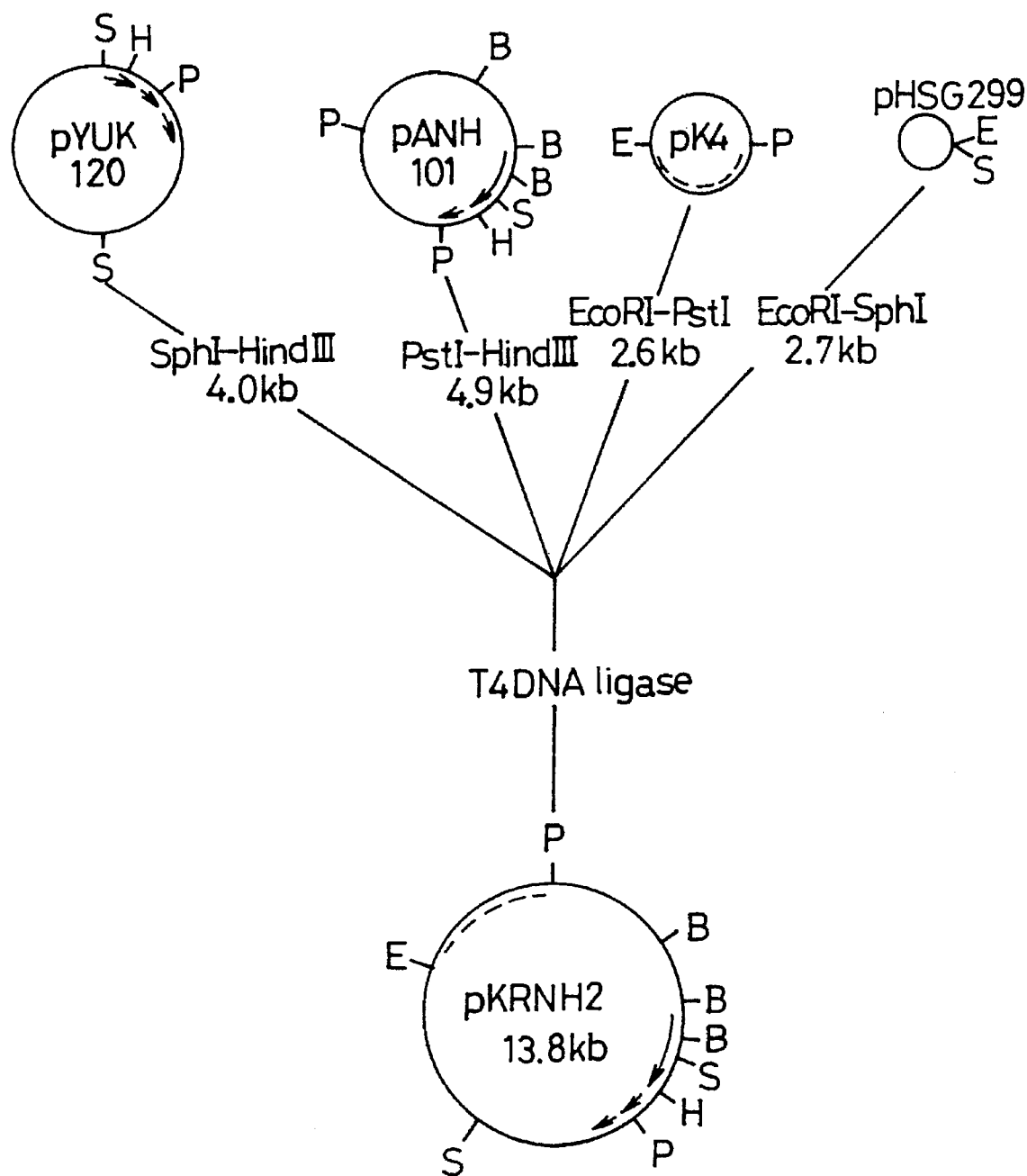
FIG. 4 shows a construction of recombinant plasmid pKRNH2.

(1)-(i) Construction of Recombinant Plasmid pKRNH2 pKRNH2 was constructed as is shown in FIG. 4. 1 µg of pYUK120 DNA was digested with SphI and HindIII to give a 4.0 kb fragment. 1 µg of pANH101 DNA was digested with PstI and HindIII to give a 4.9 kb fragment. 1 µg of pK4 DNA was digested with PstI and EcoRI to give a 2.6 kb fragment. 1 µg of pHSG299 DNA was digested with SphI and EcoRI to give a 2.7 kb fragment. The digestion reaction was carried out at 37° C. for one hour. After digestion, the reaction mixture was electrophoresed on a 0.7% agarose gel. These fragments were recoverd from the gel and purified by Gene Clean Kit (FUNAKOSHI K.K.). An equal amount of a DNA solution was taken from each purified DNA solution and was combined. T4 DNA ligase was then added to the mixture. The ligation reaction was carried out at 4° C. for 15 hours.

After the ligation reaction, the ligation product was used to transform *Escherichia coli*. JM109. Colonies were screened for white colonies by a 2xYT agar plate containing 25 µg/ml of Kanamycin, 1 mM IPTG and 0.02% X gal. Positive colonies were incubated with shaking in a 2xYT medium containing Kanamycin at 37° C. for 10 hours. Plasmid DNA was isolated from the bacterial cells, digested with restriction enzymes and analyzed. The plasmid thus obtained is designated as pKRNH2.

Figure 5:
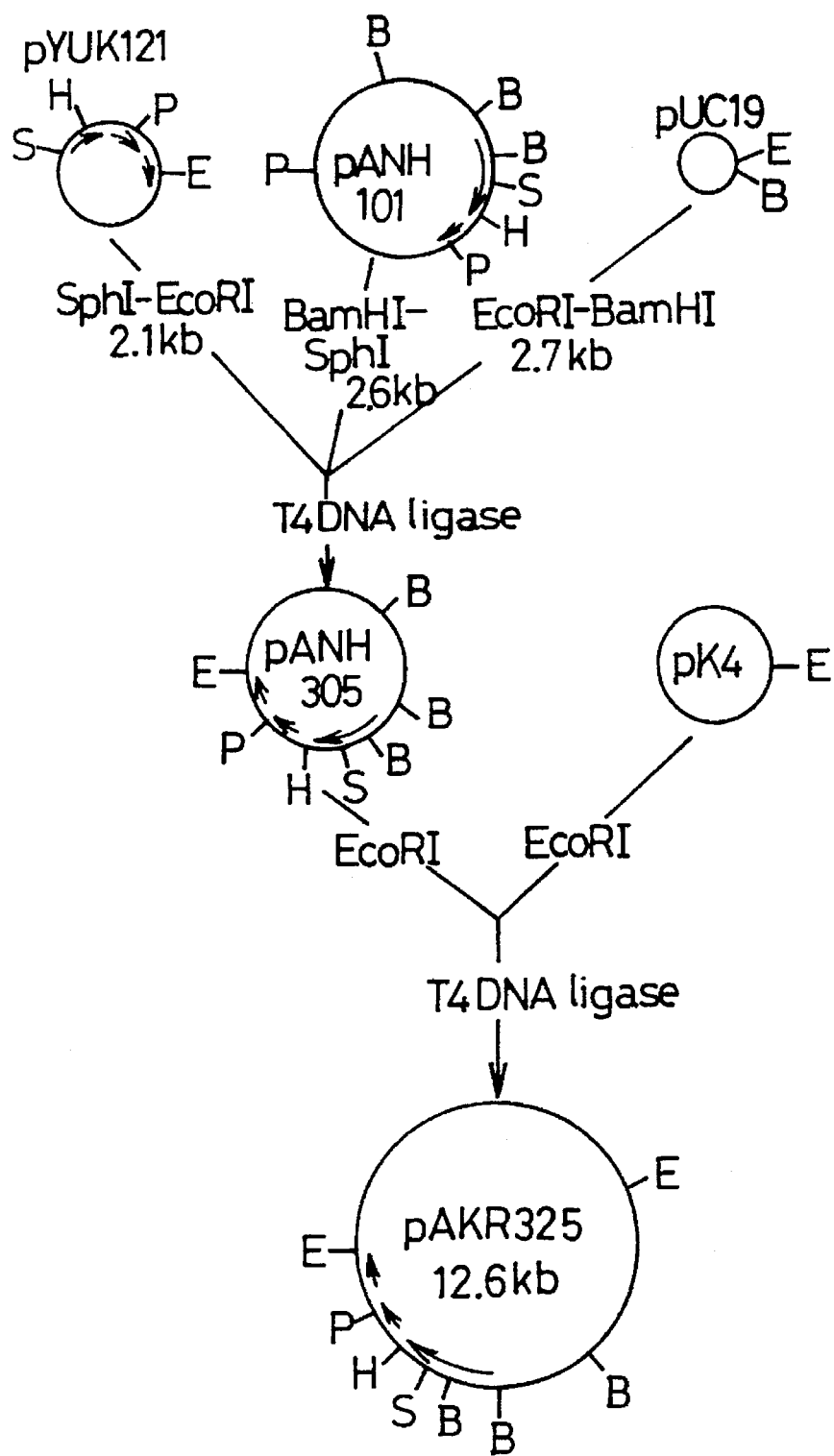
FIG. 5 shows a construction of recombinant plasmid pAKR325.

(1)–(2) Construction of Recombinant Plasmid pAKR325 pAKR325 was constructed as is shown in FIG. 5. DNA fragments were prepared and the DNA fragments were combined. T4 DNA ligase was added to the DNA mixture. After the ligation reaction, *Escherichia coli* JM 109 was transformed with the ligation product and the transformation mixture was spread on a 2xYT agar plate containing 25 µg/ml of Kanamycin, 25 µg/ml of ampicillin, 1 mM IPTG and 0.02% X gal to screen for white colonies. Positive colonies were grown in a 2xYT medium containing ampicillin and Kanamycin. Plasmid DNA was isolated from the bacterial cells, digested with restriction enzymes and analyzed. The plasmid thus obtained is designated as pAKR325.

(2) Transformation of Bacteria Belonging to the Genus Rhodococcus with pKRNH2 or pAKR325

The bacterial cells of *Rhodococcus rhodochrous* ATCC 12674 at a log phase in growth were centrifuged, washed 3 times with ice cold sterilized water and resuspended in a 15% PEG(6,000) solution (cell density: more than $10^9$ cells/ml). pKRNH2 and pAKR325, 0.01 µg each, were combined with 10 µl of the bacterial cell suspension. The mixture was incubated on ice and then placed in the chamber 11 of a cell fusion apparatus (SHIMAZU Corp., SSH-1). The chamber was cooled and the mixture was subjected to electroporation at a pulse amplitude of 500 µs at an electric field strength of 14 kv/cm.

After electroporation, the mixture was incubated on ice for 10 minutes and then at 37° C. for 5 minutes. After incubation, 1 ml of an MY medium was added to the mixture. The mixture was incubated at 25° C. for 3 hours. The mixture was then spread on an MY agar plate containing 50 µg/ml of kanamycin. The plate was incubated at 25° C. for 3–6 days. After incubation, colonies appeared on the plate. These colonies were spread on an MY agar medium plate containing 50 µg/ml of kanamycin again to confirm that the colonies were kanamycin resistant.

Transformants, each transformed with pKRNH2 or pAKR325, were deposited with Fermentation Research Institute, Agency of Industrial Science and Technology on Mar. 1, 1991, and were assigned the following accession numbers;

| | accession number |
|---|---|
| Rhodococcus rhodochrous ATCC 12674/pKRNH2 | FERM BP-3733 |
| Rhodococcus rhodochrous ATCC 12674/pAKR325 | FERM BP-3734 |

(3) Production of amides Using Transformants

Rhodococcus rhodochrous ATCC 12674/pKRNH2 (hereafter referred to as ATCC 12674/pKRNH2) and Rhodococcus rhodochrous ATCC 12674/pAKR325 (hereafter referred to as ATCC 12674/pAKR325) were grown in 10 ml of an MY-glycerol medium (1% glycerol, 0.5% polypeptone, 0.3% yeast extract, 0.3% malt extract) containing kanamycin (50 µg/ml) under the fluorescent light at 25° C. for 15–72 hours. Rhodococcus rhodochrous ATCC 12674/pK4 (hereafter referred to as ATCC 12674/pK4) was used as a control. ATCC 12674/pKRNH2, ATCC 12674/pAKR325 and the control were also grown in the same medium as described above plus 0.1% isobutyronitrile+0.1% isobutylamide as an inducer for nitrile hydratase under the same culture conditions. Bacterial cells were harvested by centrifugation, washed with 50 mM phosphate buffer/pH7.7 and resuspended in 1 ml of 50 mM phosphate buffer/pH7.7. The suspension was placed on ice under a fluorescent light for one hour. 100 µl of the suspension and 0.8 ml of 50 mM phophate buffer were combined and the mixture was then incubated at 20° C. for 10 minutes. After incubation, 10 µl of 1M acrylonitrile was added to the mixture, which was then incubated for 30 minutes. 200 µl of 1N-HCl was added to the mixture to stop the reaction. Nitrile hydratase activity was determined by measuring the amounts of acrylonitrile and acrylamide in the reaction mixture using gas chromatography. Table 3 shows the nitrile hydratase activity of the transformants and the control. The specific activity was remarkably increased by the addition of the inducer.

TABLE 3

| | | Nitrile hydratase activity | | | |
|---|---|---|---|---|---|
| | | Without inducer | | With inducer | |
| Bacterial Strain/ Plasmid | Time (hr) | Growth ($OD_{630}$) | Specific Activity (U/mg cell) | Growth ($OD_{630}$) | Specific Activity (U/mg cell) |
| ATCC 12673 /pK4 | 15 | 1.84 | 0.00 | 1.70 | 0.00 |
| | 24 | 4.66 | 0.05 | 2.27 | 0.13 |
| | 48 | 4.56 | 0.10 | 4.30 | 1.15 |
| | 72 | 4.11 | 0.03 | 6.50 | 0.06 |
| ATCC 12674 /pKRNH2 | 15 | 0.13 | 0.60 | 0.10 | 0.20 |
| | 24 | 0.20 | 1.28 | 0.05 | 25.00 |
| | 48 | 0.25 | 1.60 | 0.07 | 46.60 |
| | 72 | 1.50 | 0.12 | 0.32 | 0.44 |
| ATCC 12674 /pAKR325 | 15 | 0.33 | 0.02 | 1.09 | 0.05 |
| | 24 | 2.65 | 0.08 | 2.08 | 4.25 |
| | 48 | 4.85 | 0.13 | 3.15 | 9.01 |
| | 72 | 3.18 | 0.03 | 5.04 | 0.09 |

(4) Nitrile Hydratase Activities of the Enzyme Encoded by the Gene of Recombinant Plasmid or of Chromosome (4)-(i) SDS-gel Electrophoresis and Western-blotting Bacterial cells harvested from 10 ml of culture were washed with phosphate buffer and suspended in 1 ml of phosphate buffer. The bacterial cells were sonicated with keeping the tube containing the cells on ice and the disrupted cells were centrifuged at 15,000 rpm for 10 minutes. The supernatant containing a crude extract was used for the experiment described below. A 12.5% SDS-gel was prepared as follows. 15 ml of solution A (29.2 g of acrylamide, 0.8 g/100 ml of N,N'-methylenebisacrylamide), 9 ml of solution B (1.5M Tris-HCl/pH 8.8, 0.4% SDS) and 12 ml of distilled water were combined and the separating gel solution was subjected to degassing by an aspirator. 140 µl of 10% ammonium persulfate and 12 µl of TEMED (N,N,N',N'-tetramethylenediamine) were added to the resolving gel solution and then the separating gel solution was poured into the gap between the glass plates. Water saturated n-butanol was gently overlayed onto the surface of the gel solution and the gel was left standing until it was polymerized. In the meantime, a stacking gel solution was prepared. 1.8 ml of solution A, 3 ml of solution C (0.5M Tris-HCl/pH 6.8, 0.4% SDS) and 7.2 ml of distilled water were combined and the stacking gel solution was subjected to degassing. 36 µl of 10% ammonium persulfate and 12 µl of TEMED (N,N,N', N'-tetramethylenediamine) were added to the stacking gel solution and the stacking gel solution was mixed well. When the resolving gel solution was polymerized, the n-butanol overlay was gently discarded. The stacking gel solution was poured directly onto the resolving gel and then a comb was inserted into the stacking gel solution. When the stacking gel solution was polymerized, the gel was placed in an electrophoresis apparatus. Both upper and lower buffer reservoirs were filled with electrophoresis buffer (0.025M Tris-HCl, 0.192M glycine, 0.1% SDS). 1/3 volume of sample buffer (0.25M Tris-HCl, 4% mercaptoethanol, 8% SDS, 40% glycerol) was added to the crude extract (20 µg of protein). The mixture was heated at 90° C. for 5 minutes and then placed in the wells of the plate. Electrophoresis was carried out at 10 mA for 12–15 hours. After electrophoresis, half of the gel was stained to detect proteins and another half was used for Western blotting.

Coomassie Brilliant Blue (CBB) staining: The gel was immersed in a staining solution (0.25% CBB in a 5:1:5 water/acetic acid/methanol solution) and shaken at room temperature for one hour. The staining solution was decanted. The gel was rinsed with water briefly and washed in a 8:1:1 water/methanol/acetic acid solution at room temperature for 24 hours.

Western blotting: A rabbit antiserum specific to nitrile hydratase purified from Rhodococcus sp. N-774 was used as a primary antibody. The proteins on the gel were transferred to a transfer membrane [Poly(vinylidene difluoride), Millipore] using zaltoblot 2-SM17556. The transfer was carried out at 4 mA/cm$^2$ for 15 minutes. The transfer membrane was soaked in 100 ml of TBS containing 3 g of heat dissolved gelatin. The membrane was incubated with shaking at room temperature for one hour. The membrane was then transferred to 100 ml of TBS solution containing 1% gelatin: 20 µl of the primary antibody was added to the solution and the membrane was incubated with shaking at room temperature for 2 hours. After incubation, the membrane was washed 2 times with TBS and then placed in 100 ml of TBS containing 1% gelatin. 50 µl of a secondary antibody, goat anti-rabbit IgG horseradish peroxidase (GAR-HRP)[Bio-Rad], was added to the TBS. The membrane was incubated with shaking at room temperature for 2 hours. The membrane was washed with distilled water and then 2 times with TBS. The membrane was placed in 100 ml of TBS containing 60 µl of $H_2O_2$ in a vessel. 60 mg of a HRP color development reagent (BiO-Rad) dissolved in 20 ml of ice cold methanol was added to the vessel. When the band appeared on the membrane, the membrane was washed with distilled water and dried.

Almost no nitrile hydratrase band was found on the gel stained by CBB. However in the ATCC12674/pKRNH2 lane and the ATCC12674/pAKR325 lane on the gel of Western blotting, bands resulting from the binding of the antibody to nitrile hydratase were found at the same position as the one of the band of nitrile hydratase obtained from *Rhodococcus sp.* N-774. In contrast, there was no band found in the control lane (*Rhodococcus rhodochrous*/pK4). ATCC 12674/pKRNH2 and ATCC12674/pAKR325 were found to express the nitrile hydratase gene derived from *Rhodococcus sp.* N-774.

(4)-(ii) Photoactivation of Nitrile Hydratase

Nitrile hydratase of *Rhodococcus sp.* N-774 is known to be activated by light illumination while the photoactivation of the nitrile hydratase of *Rhodococcus rhodochrous* ATCC 12674 is not known. It is possible to confirm that whether ATCC12674/pKRNH2 and ATCC12674/pAKR325 express the nitrile hydratase gene derived from *Rhodococcus sp.* N-774 by the photoactivation.

10 ml of an MY-glycerol medium was placed in a test tube and the tube was autoclaved. ATCC 12674/pk4, ATCC 12674/pKRNH2 and ATCC12674/pAKR325 were placed in a separate tube and grown without exposing to light (the tube was wrapped by aluminum foil) or under the exposure to light. Both cultures were incubated with shaking at 26° C. for 36 hours. After incubation, the nitrile hydratrase activity was determined. The bacterial cells grown under dark conditions were manipulated only in dark conditions: centrifugation was carried out under a weak red light in the darkroom. ATCC12674/pK4 (control) did not show photoactivation while ATCC 12674/pKRNH2 and ATCC 12674/pAKR325 increased enzyme activity, under the exposure to light. The result suggested that ATCC12674/pKRNH2 and ATCC12674/pAKR325 produced an enzyme having a photoactivation shown by *Rhodococcus sp.* N-774.

TABLE 4

Photoactivation of Nitrile hydratase

| Bacterial Strain/ Plasmid | Dark conditions | | Light conditions | |
|---|---|---|---|---|
| | Growth (OD$_{630}$) | Specific Activity (U/mg cell) | Growth (OD$_{630}$) | Specific Activity (U/mg cell) |
| ATCC 12674 /pK4 | 9.0 | 1.2 | 6.5 | 1.4 |
| ATCC 12674 /pKRNH2 | 0.08 | 96.8 | 0.18 | 193 |
| ATCC 12674 /pAKR325 | 14.5 | 0.3 | 13.8 | 1.7 |

Example 4

Production of Amides Using Transformants

*Rhodococcus rhodochrous* ATCC 12674/pKRNH2 (hereafter referred to as ATCC 12674/pKRNH2) was grown in 10 ml of an MYP medium (1% glycerol, 0.5% polypeptone, 0.3% yeast extract, 0.3% malt extract, 0.05% potassium dihydrogenphosphate, 0.05% dipotassium hydrogenphosphate, 50 µg/ml of kanamycin) in the presence of a given amount of methacrylamide, an inducer for nitrile hydratrase, or in the absence of the inducer agent, under the fluorescent light at 25° C. for 24–48 hours. *Rhodococcus rhodochrous* ATCC 12674/pK4 (hereafter referred to as ATCC 12674/pK4) used as a control was also grown under the same culture conditions. Bacterial cells were harvested by centrifugation, washed with 50 mM phosphate buffer/pH7.7 and resuspended in 1 ml of 50 mM phosphate buffer/pH7.7. The suspension was placed on ice under the fluorescent light for one hour. 100 µl of the suspension and 0.8 ml of 50 mM phosphate buffer were combined and the mixture was then incubated at 20° C. for 10 minutes. After incubation, 10 µl of 1M acrylonitrile was added to the mixture, which was then incubated for 10 minutes. 200 µl of 1N-HCl was added to the mixture to stop the reaction. Nitrile hydratase activity was determined by measuring the amount of acrylonitrile and acrylamide in the reaction mixture using gas chromatography. Table 5 shows the nitrile hydratase activity of ATCC12674/pKRNH2 and the control.

TABLE 5

Nitrile hydratase activity

| Bacterial Strain/ Plasmid | Methacrylamide | Growth (OD$_{630}$) | Specific Activity (U/mg cell) |
|---|---|---|---|
| ATCC 12673 /pK4 | 0 | 3.2 | trace |
| | 0.1 | 3.1 | 3.2 |
| | 0.2 | 3.6 | 9.1 |
| ATCC 12674 /pKRNH2 | 0 | 2.7 | 12.1 |
| | 0.1 | 2.5 | 45.0 |
| | 0.2 | 2.1 | 152.3 |

Example 5

Production of Acids Using Transformants

*Rhodococcus rhodochrous* ATCC 12674/pKRNH2 (hereafter referred to as ATCC 12674/pKRNH2) was grown in 10 ml of an MYP medium (1% glycerol, 0.5% polypeptone, 0.3% yeast extract, 0.3% malt extract, 0.05% potassium dihydrogenphosphate, 0.05% dipotassium hydrogenphosphate 50 µg/ml of kanamycin) in the presence of a given amount of methacrylamide, an inducer for amidase, or in the absence of the inducer, under the fluorescent light at 25° C. for 24–48 hours. *Rhodococcus rhodochrous* ATCC 12674/pK4 (hereafter referred to as ATCC 12674/pK4) used as a control was also grown under the same culture conditions. Bacterial cells were harvested by centrifugation, washed with 50 mM phosphate buffer/pH7.7 and resuspended in 1 ml of 50 mM phosphate buffer/pH7.7. The suspension was incubated on ice under the fluorescent light for one hour. 100 µl of the suspension and 0.8 ml of 50 mM phophate buffer were combined and the mixture was then incubated at 20° C. for 10 minutes. After incubation, 100 µl of 1M propionamide was added to the mixture, which was then incubated for 1 hour. 200 µl of 1N-HCl was added to the mixture to stop the reaction. Amidase activity was determined by measuring an amount of propionamide and propionic acid in the reaction mixture using gas chromatography. Table 6 shows the amidase activity of ATCC12674/pKRNH2 and the control.

TABLE 6

| Bacterial Strain/ Plasmid | amidase activity | | |
|---|---|---|---|
| | Methacrylamide | Growth (OD$_{630}$) | Specific Activity (U/mg cell) |
| ATCC 12673 | 0 | 3.2 | 0.03 |
| | 0.1 | 3.1 | 0.04 |
| /pK4 | 0.2 | 3.6 | 0.05 |
| ATCC 12674 | 0 | 2.7 | 0.10 |
| | 0.1 | 2.5 | 0.50 |
| /pKRNH2 | 0.2 | 2.1 | 1.49 |

What is claimed is:

1. A hybrid plasmid vector comprising:

(A) a first isolated DNA sequence which is derived from a plasmid selected from the group consisting of pRC001, pRC002, pRC003 and pRC004, and which confers on the vector the ability to replicate and amplify in *Rhodococcus rhodochrous*;

(B) a second isolated DNA sequence which confers on the vector the ability to replicate and amplify in *Escherichia coli*; and (C) a third isolated DNA sequence containing a drug resistance gene for the drug kanamycin.

2. The hybrid plasmid vector of claim 1 in which the second isolated DNA sequence is isolated from a plasmid selected from the group consisting of pHSG299, pHSG298, pUC19 and pUC18.

3. The hybrid plasmid vector of claim 1 comprising pK1, pK2, pK3, pK4 or pA3.

4. A transformed cell comprising a bacterial cell of the genus Rhodococcus or Escherichia transformed with a hybrid plasmid vector according to any one of claims 1–3.

5. The transformed cell of claim 4 which is a cell of *Rhodococcus rhodochrous* ATCC 12674.

6. The transformed cell of claim 4 which is a cell of *Escherichia coli* K-12.

7. A recombinant plasmid comprising:

(a) a hybrid plasmid vector according to claim 1; and (b) an additional isolated DNA sequence of one or more genes encoding a nitrile hydratase and an amidase which additional sequence is derived from a bacterium of the genus Rhodococcus and expresses nitrile hydratase activity, amidase activity or both in a bacterium of the genus Rhodococcus.

8. A recombinant plasmid comprising:

(a) a hybrid plasmid vector according to claim 2; and (b) an additional isolated DNA sequence of one or more genes encoding a nitrile hydratase and an amidase which additional sequence is derived from a bacterium of the genus Rhodococcus and expresses nitrile hydratase activity, amidase activity or both in a bacterium of the genus Rhodococcus.

9. A recombinant plasmid comprising:

(a) a hybrid plasmid vector according to claim 3; and (b) an additional isolated DNA sequence of one or more genes encoding a nitrile hydratase and an amidase which additional sequence is derived from a bacterium of the genus Rhodococcus and expresses nitrile hydratase activity, amidase activity or both in a bacterium of the genus Rhodococcus.

10. A recombinant plasmid comprising:

(a) a hybrid plasmid vector which comprises i. a first isolated DNA sequence which confers on the vector the ability to replicate and amplify in *Rhodococcus rhodochrous*, ii. a second isolated DNA sequence which confers on the vector the ability to replicate and amplify in *Escherichia coli*, and iii. a third isolated DNA sequence containing a drug resistance gene; and (b) an additional isolated DNA sequence of one or more genes encoding a nitrile hydratase and an amidase which additional sequence is derived from a bacterium of the genus Rhodococcus and expresses nitrile hydratase activity, amidase activity or both in a bacterium of the genus Rhodococcus.

11. A bacterial cell of the genus Rhodococcus which is transformed with a recombinant plasmid according to any one of claims 7–10.

12. A method of producing an amide compound which comprises:

(a) culturing the bacterial cell of claim 11 with an amide inducer such that nitrile hydratase is expressed, and (b) contacting the bacterial cell with a nitrile compound at a concentration of 0.1 (w/v) % to 10 (w/v) % at pH 4 to pH 10 such that the nitrile compound is hydrated to a corresponding amide compound.

13. A method of producing an acid compound which comprises:

(a) culturing the bacterial cell of claim 11 with an amide inducer such that nitrile hydratase and amidase are expressed, and (b) contacting the bacterial cell with a nitrile or amide compound at a concentration of 0.1 (w/v) % to 10 (w/v) % at pH 4 to pH 10 such that the nitrile or amide compound is hydrolyzed to a corresponding acid compound.

14. The method of producing an amide compound according to claim 12, which, after step (a) and before step (b), further comprises the step of incubating the bacterial cell at about 4° C. with fluorescent light.

15. The method of producing an acid compound according to claim 13, which, after step (a) and before step (b), further comprises the step of incubating the bacterial cell at about 4° C. with fluorescent light.

16. A method of producing an amide compound which comprises:

(a) culturing the bacterial cell of claim 11 with an amide inducer such that the nitrile hydratase is expressed, (b) preparing a lysate or extract of the bacterial cell, and (c) contacting the lysate or extract with a nitrile compound at a concentration of 0.1 (w/v) % to 10 (w/v) % at pH 4 to pH 10 such that the nitrile compound is hydrated to a corresponding amide compound.

17. The method of producing an amide compound according to claim 16, which, after step (a) and before step (b), further comprises the step of incubating the bacterial cell at about 4° C. with fluorescent light.

18. A method of producing an acid compound which comprises:

(a) culturing the bacterial cell of claim 11 with an amide inducer such that the nitrile hydratase and amidase are expressed, (b) preparing a lysate or extract of the bacterial cell, and (c) contacting the lysate or extract with a nitrile or amide compound at a concentration of 0.1 (w/v) % to 10 (w/v) % at pH 4 to pH 10 such that the nitrile or amide compound is hydrolyzed to a corresponding acid compound.

19. The method of producing an acid compound according to claim 18, which, after step (a) and before step (b), further comprises the step of incubating the bacterial cell at about 4° C. with fluorescent light.

* * * * *